(12) United States Patent
Imran

(10) Patent No.: US 10,398,904 B2
(45) Date of Patent: *Sep. 3, 2019

(54) ENERGY HARVESTING MECHANISM FOR MEDICAL DEVICES

(71) Applicant: InCube Labs, LLC, San Jose, CA (US)

(72) Inventor: Mir A. Imran, Los Altos Hills, CA (US)

(73) Assignee: InCube Labs, LLC, San Jose, CA (US)

( * ) Notice: Subject to any disclaimer, the term of this patent is extended or adjusted under 35 U.S.C. 154(b) by 15 days.

This patent is subject to a terminal disclaimer.

(21) Appl. No.: 15/440,835

(22) Filed: Feb. 23, 2017

(65) Prior Publication Data

US 2017/0197085 A1 Jul. 13, 2017

Related U.S. Application Data

(63) Continuation of application No. 14/678,801, filed on Apr. 3, 2015, now Pat. No. 9,616,242, which is a (Continued)

(51) Int. Cl.
*A61N 1/37* (2006.01)
*A61N 1/39* (2006.01)
(Continued)

(52) U.S. Cl.
CPC ........... *A61N 1/3785* (2013.01); *A61N 1/362* (2013.01); *A61N 1/3702* (2013.01); *A61N 1/3956* (2013.01)

(58) Field of Classification Search
CPC .... A61N 1/3785; A61N 1/362; A61N 1/3702; A61N 1/3956
See application file for complete search history.

(56) References Cited

U.S. PATENT DOCUMENTS

| 3,456,134 A | 7/1969 | Wen |
| 3,563,245 A | 2/1971 | McLean et al. |

(Continued)

FOREIGN PATENT DOCUMENTS

| JP | 2004-115655 | 2/2004 |
| JP | 2007-281015 | 10/2007 |

(Continued)

OTHER PUBLICATIONS

First examination Report dated Oct. 3, 2013 in Australian Application 2009298928.

(Continued)

*Primary Examiner* — Catherine M Voorhees
(74) *Attorney, Agent, or Firm* — Mahamedi IP Law LLP; Joel Harris

(57) ABSTRACT

Embodiments of the invention provide apparatus, systems and methods for harvesting energy from bio-kinetic events to power various implanted medical devices. One embodiment provides an energy harvesting mechanism for a cardiac pacemaker comprising an energy converter and a signal path component. The energy converter is positionable inside a human body and configured to generate electric power signals in response to a bio-kinetic event of the human body such as a heart beat, respiration or arterial pulse. The converter can comprise a piezoelectric material which generates electricity in response to mechanical deformation of the converter. The converter can also have a power generation characteristic that is matched to the frequency of the bio-kinetic event. For heart beat powered applications, the power generation characteristic can be matched to the physiologic range of pulse rates.

14 Claims, 14 Drawing Sheets

Related U.S. Application Data continuation of application No. 12/561,159, filed on Sep. 16, 2009, now Pat. No. 9,026,212.

(60) Provisional application No. 61/099,203, filed on Sep. 23, 2008.

(51) Int. Cl.
*A61N 1/362* (2006.01)
*A61N 1/378* (2006.01)

(56) References Cited

U.S. PATENT DOCUMENTS

| | | | |
|---|---|---|---|
| 3,693,625 A | 9/1972 | Auphan | |
| 4,613,784 A | 9/1986 | Haun et al. | |
| 4,690,143 A | 9/1987 | Schroeppel | |
| 4,780,638 A | 10/1988 | Reinelt et al. | |
| 4,798,206 A | 1/1989 | Maddison et al. | |
| 5,431,694 A | 7/1995 | Snaper et al. | |
| 5,615,466 A | 4/1997 | Safari et al. | |
| 5,869,189 A | 2/1999 | Hagood et al. | |
| 6,131,581 A | 10/2000 | Leysieffer et al. | |
| 6,337,835 B1 | 1/2002 | Sporn et al. | |
| 6,822,343 B2 | 11/2004 | Estevez | |
| 6,963,157 B2 | 11/2005 | Sato et al. | |
| 7,084,605 B2 | 8/2006 | Mickle et al. | |
| 7,130,681 B2 | 10/2006 | Gebhardt et al. | |
| 7,142,075 B1* | 11/2006 | Roesler | H02K 35/02 |
| | | | 200/181 |
| 7,292,888 B2 | 11/2007 | Deno et al. | |
| 7,365,455 B2 | 4/2008 | Hamel et al. | |
| 7,629,727 B2 | 12/2009 | Whinnery | |
| 8,311,632 B2 | 11/2012 | Pless et al. | |
| 8,948,870 B2 | 2/2015 | Imran | |
| 9,026,212 B2* | 5/2015 | Imran | A61N 1/3785 |
| | | | 607/35 |
| 9,616,242 B2* | 4/2017 | Imran | A61N 1/3785 |
| 2002/0053801 A1 | 5/2002 | Herman | |
| 2003/0056351 A1 | 3/2003 | Wilkie et al. | |
| 2003/0141785 A1 | 7/2003 | Sato et al. | |
| 2004/0073267 A1 | 4/2004 | Holzer | |
| 2005/0012434 A1 | 1/2005 | Pizzochero et al. | |
| 2005/0110277 A1 | 5/2005 | Adamson et al. | |
| 2005/0274176 A1 | 12/2005 | Thiesen et al. | |
| 2006/0184206 A1 | 8/2006 | Baker et al. | |
| 2006/0217776 A1 | 9/2006 | White et al. | |
| 2007/0078492 A1 | 4/2007 | Piergiorgio et al. | |
| 2007/0088402 A1 | 11/2007 | Fortune et al. | |
| 2007/0293904 A1 | 12/2007 | Gelbart et al. | |
| 2008/0119421 A1 | 5/2008 | Tuszynski et al. | |
| 2008/0136292 A1 | 6/2008 | Thiesen | |
| 2008/0150396 A1 | 6/2008 | Clingman | |
| 2008/0200963 A1 | 8/2008 | Pless et al. | |
| 2008/0203849 A1 | 8/2008 | Hagg | |
| 2008/0262562 A1* | 10/2008 | Roberts | A61N 1/3785 |
| | | | 607/35 |
| 2009/0152990 A1 | 6/2009 | Brown et al. | |
| 2009/0167034 A1 | 7/2009 | Waters et al. | |
| 2009/0167110 A1 | 7/2009 | Berkcan et al. | |
| 2009/0171448 A1 | 7/2009 | Eli | |
| 2009/0216292 A1* | 8/2009 | Pless | A61N 1/3785 |
| | | | 607/33 |
| 2010/0049269 A1 | 2/2010 | Tran et al. | |
| 2010/0063557 A1 | 3/2010 | Imran | |
| 2010/0076517 A1 | 3/2010 | Imran | |
| 2010/0171394 A1 | 7/2010 | Glenn et al. | |
| 2010/0331915 A1* | 12/2010 | Hill | A61N 1/37217 |
| | | | 607/60 |

FOREIGN PATENT DOCUMENTS

| | | |
|---|---|---|
| JP | 2007-529456 | 10/2007 |
| JP | 2008-516739 | 5/2008 |
| JP | 2009-529975 | 8/2009 |
| WO | WO 2006/024868 A2 | 3/2006 |
| WO | WO 2007/068284 | 6/2007 |
| WO | WO 2007/109272 A2 | 9/2007 |
| WO | WO 2007/149462 A2 | 12/2007 |
| WO | WO 2008/085886 A2 | 7/2008 |
| WO | WO 2010/039497 | 4/2010 |

OTHER PUBLICATIONS

Second Examination Report dated Oct. 1, 2013 in European Application 09818246.2.
Second Office Action dated Jul. 23, 2013 in Chinese Application No. 200980142008.9.
First Office Action dated Sep. 24, 2013 in Japanese Application No. 2011-529162.
Nissi, "Fast Heart Rate (more than 100 beats per minute) without obvious cause." Apr. 27, 2007, WebMD: http/www.webmd.com/a-to-z-guieds/fast-heart-rate-more-than-100-beats-per-minute-without-obvious-cause.
First Examination Report dated Jan. 23, 2013 in European Application No. 09818246.2.
International Preliminary Report on Patentability dated Mar. 29, 2011 in International Application No. PCT/US2009/057855.
Office Action dated Aug. 31, 2012 in corresponding Chinese Application 200980142008.9.
International Search Report and Written Opinion dated May 3, 2010 in International Application No. PCT/US2009/057855.
International Search Report and Written Opinion dated Feb. 2, 2010 in International Application No. PCT/US2009/056402.
Office Action dated Aug. 11, 2015 in corresponding Japanese Application 2014197996.

* cited by examiner

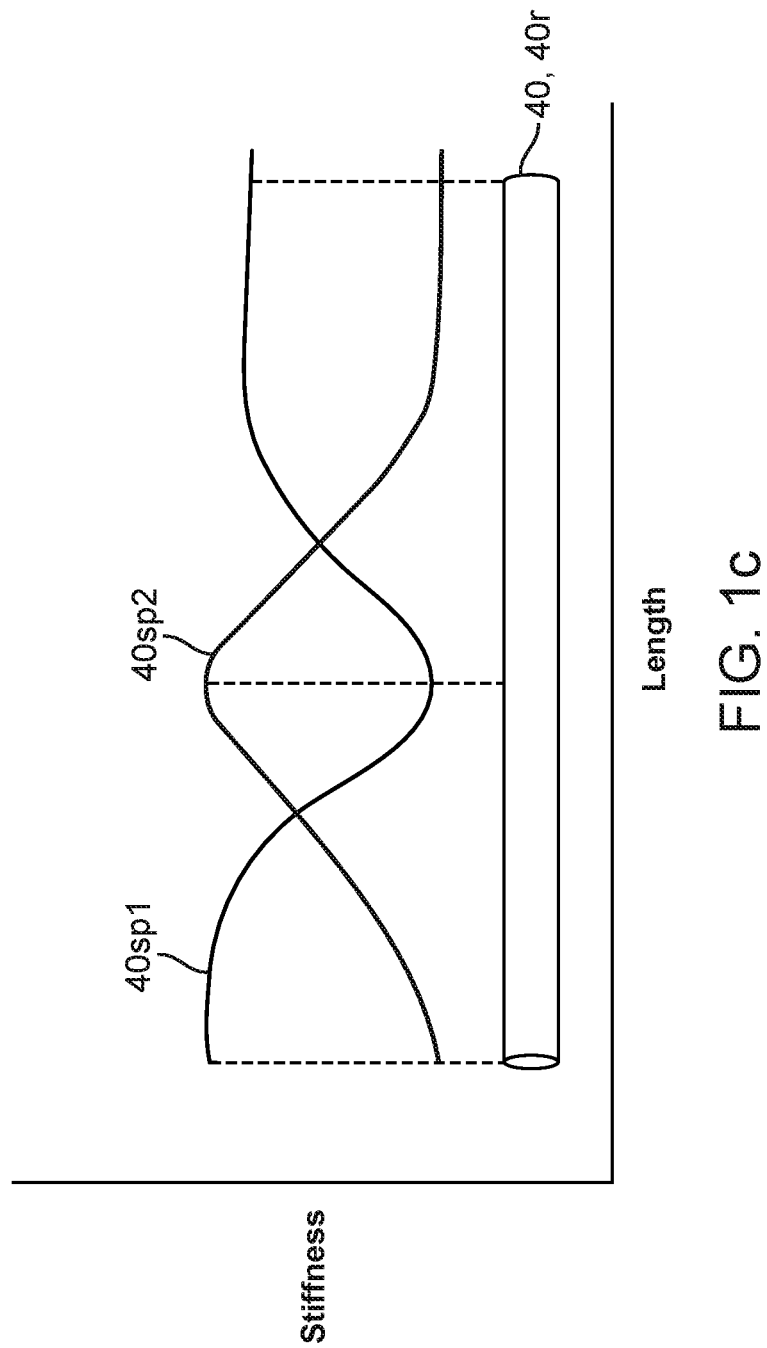

20 Implanted Device
40 Converter
110 DC-DC Converter

ENERGY HARVESTING MECHANISM FOR MEDICAL DEVICES

RELATED APPLICATIONS

This application is a continuation of U.S. patent application Ser. No. 14/678,801 entitled "ENERGY HARVESTING MECHANISM FOR MEDICAL DEVICES", filed Apr. 3, 2015, which is a continuation of U.S. patent application Ser. No. 12/561,159 entitled "ENERGY HARVESTING MECHANISM FOR MEDICAL DEVICES", filed Sep. 16, 2009, which application claims the benefit of Provisional U.S. Patent Application No. 61/099,203, filed Sep. 23, 2008, entitled ENERGY HARVESTING MECHANISM FOR MEDICAL DEVICES. The aforementioned applications are hereby incorporated by reference in their entirety.

BACKGROUND OF THE INVENTION

Field of the Invention

Embodiments of the invention relate to energy harvesting mechanisms. More specifically, embodiments of the invention relate to the use of energy harvesting mechanisms for powering implanted medical devices such as pacemakers, defibrillators and other devices.

A number of implantable electronic medical devices such as cardiac pacemakers and implantable defibrillators utilize a battery power source. The operational life of many of these devices is limited by the life of the battery. While there have been many advances in portable battery technology, most current devices do not last longer than ten years at which time, the pace maker must be removed. Also, many batteries undergo a certain amount of self-discharge so even if the pacemaker or other devices is not drawing current battery failure will still occur over time. Battery failure can be sudden or occur through a drop off in battery voltage. Whatever the cause, battery failure can be a life threatening event requiring immediate intervention including surgery. Thus there is a need for improved power sources for cardiac pacemakers and other implanted medical devices

BRIEF SUMMARY OF THE INVENTION

Embodiments of the invention provide apparatus, systems and methods for harvesting energy from biokinetic events to power various implanted medical devices. One embodiment provides an energy harvesting mechanism for a cardiac pacemaker comprising an energy converter and a signal path component. The energy converter is positionable inside a human body and configured to generate electric power signals in response to a bio-kinetic event of the human body such as a heart beat, respiration or arterial pulse. The converter can also have a peak generated voltage or other power generation characteristic (e.g., root mean square generated voltage or voltage), that is matched to the frequency of the bio-kinetic event. For heart beat powered applications, the power generation characteristic can be matched to the typical physiologic range of pulse rates, e.g., 40 to 180 beats per minute. It can also be matched to the pulse range for a particular patient. As is explained below, the converter can also be configured to generate electricity for deformation in any or all three axis's. Also, the energy converter can be figured to generate electric power independent of a plane of deformation of the converter.

Typically, the current generated by deformation of the converter is AC, but it can be rectified to generate DC. The converter can be sized or otherwise configured to generate sufficient electrical power to power the entire pacemaker (or other device) or to supplement the current from a pacemaker battery, allowing for longer battery life as well as providing a backup should the battery fail. Power management circuitry can be used to switch between use of battery power or the converter as the power supply as well as charge the battery by a trickle charge or other charging regimen. In particular embodiments, the converter can be configured to generate between 20 to 40 µamps of current.

In many embodiments, the energy converter comprises a piezoelectric material which generates electricity in response to mechanical deformation of the converter. The converter is desirably positioned to deform in response to motion from the heartbeat or other bio-kinetic event so that with each heartbeat, the converter generates electrical power to power the pacemaker. The thickness and material properties of the converter can be configured to have a stiffness/flexibility which allows for a peak generated voltage, current etc, for a frequency of converter deformation within the physiological range of pulse rates. They can also be configured so the converter has a resonant frequency within this range of these pulse rates.

In many embodiments, the piezo-electric material comprises a bundle of piezo-electric fibers which are arranged around a core conductor. The piezo electric fibers are of a sufficient number and arrangement such that when the bundle is deformed in a given direction at least one fiber will be deformed sufficiently to generate sufficient energy for the pacemaker or other selected device. Thus, the bundle can generate voltage from deformation in any direction as opposed to only one or a limited number of directions.

The signal path component is structured to enable the power signals to be carried from the energy converter to the cardiac pacemaker. In many embodiments, the signal path component comprises a cable or lead that carries pace making signals to the heart. Typically, the energy converter will be positioned in the cable so that movement of the cable from the beating heart provides the kinetic energy for energy conversion. Other configurations are also contemplated, such as attaching the converter to the cable or to a container housing the pacemaker electronics.

The cable or lead can include at least a first wire for carrying the pacemaker signal to the heart and at least a second wire for carrying power signals to the pacemaker. Typically, the energy converter is shaped to fit within cable. The converter can be coaxial with respect to the cable and can have a form factor or shape that does not change the form factor of the cable. In this way, no additional volume is required for integrating the converter into the cable.

In a preferred embodiment, the converter can have a rod or cylindrical shape in a non-deformed state. In such embodiments, bending or flexing of the rod provides the deformation that causes energy generation. The stiffness of the rod can be configured to cause selectable amounts of bending and produce a particular maximum voltage for a given frequency of deformation from a heart beat or other bio-kinetic event. The rod or other shaped converter can also be configured to generate voltage from multiple types of deformation such as bending twisting, pulling, compression and combinations therefore.

The rod can also be tapered, articulated, crimped or otherwise configured to bend at particular location or locations on the rod so as to generate the maximum amount of voltage. In particular embodiments, the rod can have a stiffness profile configured to optimize the generation of electric current depending the position of the lead in the heart, position of the converter in the lead, heart rate or other factor. Stiffer profiles can be selected for locations likely to produce greater amounts of deformation and versa visa. All or a portion of the rod can also be pre-shaped to have a curved or other shape with spring memory so that rod will bend from motion of the heart or other bio-kinetic event and then spring back to its original shape. The shape of the curve can match a shape of the ventricle in its contracted or expanded state so that electrical energy can be generated during systole, diastole or both.

The portion of the cable or lead containing the energy converter is desirably placed on, in or near the heart so that it is flexed or otherwise moved by the motion of the heart. The energy converter can also be placed in a selected location in the lead so as generate a selectable amount of current from deformation of the lead. For example, the converter can placed in a portion of the cable lead is positioned on or near the apex of the heart. The lead can also include multiple energy converter portions, positioned at selectable locations in the lead so as to have multiple locations for energy generation. The lead can also be tapered or articulated so as to bend or otherwise deform at the particular locations where the energy converter is positioned. In some embodiments, the energy converter can even be embedded into the heart wall (e.g., using a helical or other anchor) so as to be deformed during motion of the heart.

In another aspect of the invention, a rechargeable power supply can be coupled to a wire, cable or other signal path component and configured to receive electrical energy generated by the energy converter. In various embodiments, the power supply can include a rechargeable battery, capacitor or other electrical storage means. In these and related embodiments, the power supply can be configured to provide power for a selectable period should the patient's heart stop or develop an arrhythmia, other rhythm abnormality (e.g., fibrillation) or other condition which prevents adequate power generation for pacing or other function. The rechargeable power supply can also be used to perform a secondary function such as defibrillation. Power management circuitry and regimens can be employed to recharge the power supply while still maintaining sufficient current and voltage for pacing. In one embodiment, a trickle charge regimen can be used. A duty cycle approach can also be employed to divert power during portions of the cardiac cycle that do not require pacing. In other embodiments, EKG monitoring circuitry can be used to determine when pacing is not required and then send a signal to the power management circuitry to divert power to the rechargeable power supply. A combination of these approaches can also be employed.

In still another aspect of the invention, embodiments of the energy converter can also be used as a sensor to sense various mechanical and electrical properties of the heart including heart rate, rhythm (e.g., normal sinus rhythm, arrhythmia, pvc, etc.), wall motion abnormalities, myopathy, ventricular hypertrophy and related condition. One or more of these conditions can be detected through means of an algorithm that analyzes one or more of voltage, current or power wave forms generated by the energy converter. Specifically the algorithm can be configured to detect changes in amplitude, frequency of the wave form or both. When amplitude (voltage or current) or frequency falls below a threshold a signal can be sent to a controller, power management circuitry or telemetry circuitry to alert the patient or a medical professional. Changes can also be detected using derivative or integral functions. For example, a derivative function can be used to look for rates of change in amplitude. An integral function can be used on one or more curves, for example to look for changes in total work done over time. Energy converters can also be configured and positioned to sense other bio-kinetic data such as respiration rate, blood pressure, heart valve function and other related functions.

Embodiments of the energy converter can be configured to simultaneously perform energy harvesting and sensing. Multiple converters can be placed in one or more pacemaker leads so as to sense in one or more locations to create a map of heart wall motion, rhythm or other cardiac function or property. Similar approaches can be used to map the motion of other bio-kinetic events such as respiration, peristaltic waves or other digestive motion, arterial pulsation and like motions. Further details of these and other embodiments and aspects of the invention are described more fully below with reference to that attached figures.

BRIEF DESCRIPTION OF THE DRAWINGS

FIG. 1c is a graph illustrating a stiffness profile for a rod shaped embodiment of the energy converter

DETAILED DESCRIPTION OF THE INVENTION

Figure 1A:
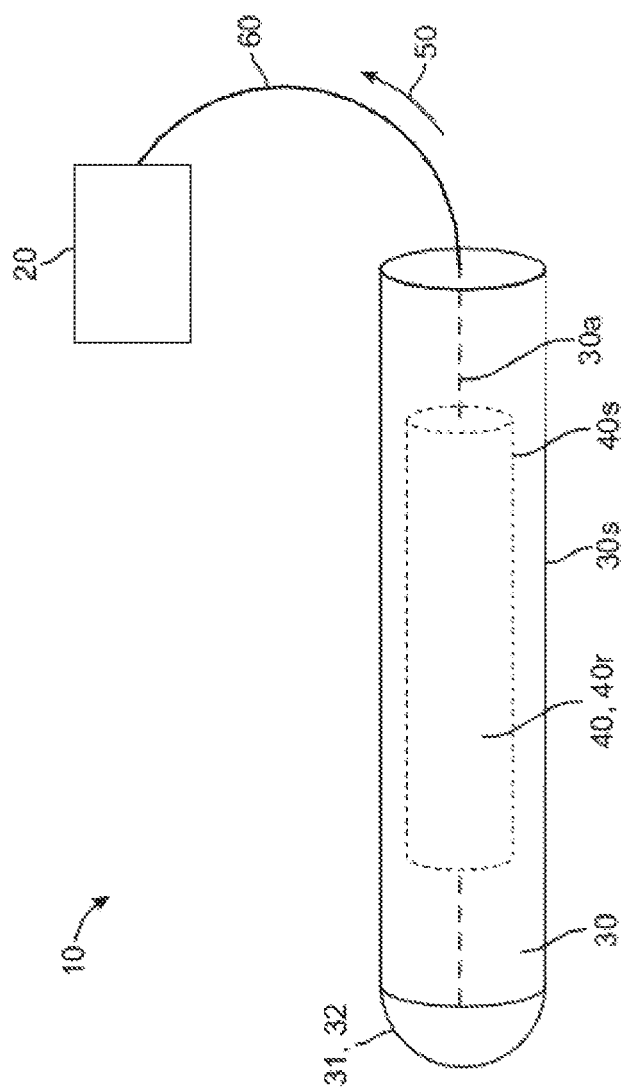
FIG. 1a is a lateral view showing an embodiment of an energy harvesting system for a pacemaker or other cardiac device.
Figure 1B:
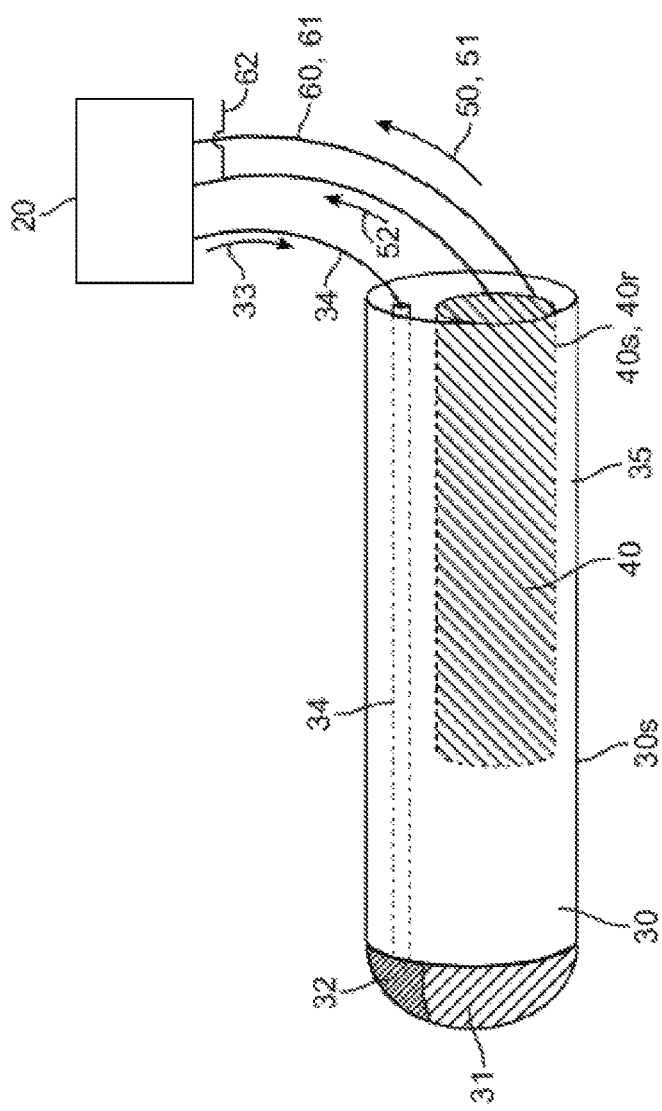
FIG. 1b is a lateral view showing the electrical connections and signal direction for a cardiac device energy harvesting system.

Embodiments of the invention provide apparatus, systems and methods for using energy harvesting materials, such as piezo electric materials, to power various implanted electronic medical electronic devices such as implantable cardiac pace maker devices. Referring now to FIGS. 1a-1b, one embodiment of an energy harvesting system 10 for powering an implanted cardiac pacemaker, or other electronic medical device 20 includes a cable 30 having an energy converter 40 that sends electrical power signals 50 via a signal path component 60 such as a wire. In various embodiments, device 20 can comprise an implantable cardiac defibrillator, cardiac telemetry device, cardiac assist device, and/or an implantable pump (e.g., an insulin pump). For ease of discussion, the following description of various embodiments of system 10 will be referring to device 20 as an implanted cardiac pacemaker 20. Such embodiments will also be referring to cable 30 as a cardiac lead 30. However, it should be understood that system 10 can be readily adapted for use with one or more other devices 20 and cables 30.

Lead 30 has a distal end 31 which includes an electrode 32 for providing a pacing signal 33 via one or more dedicated pacemaker wires 34 within lead 30. The lead also has one or more wires which serve as signal path components 60 for sending a power signal 50 to the pacemaker or other device 20. In specific embodiments, the lead can include a first and second wire 61 and 62 for sending a first and second power signal 51 and 52, for example one higher voltage and one lower voltage so as to power different components of device 20 or another device (not shown). Wires 60 can also be used for sending signals 50 to converter 40, for example, to activate one or more switches within the converter (not shown) to dynamically reconfigure the power generation characteristics of the converter. A portion of wires 60 can comprise the core conductor of fiber bundle 42 described below.

Energy converter 40 converts mechanical energy into electrical energy and when placed in proximity to various moving body tissues or structures and can be used to harvest energy from the movement of those tissues/structures caused by a biokinetic event such as heart beat (thus, energy converter 40 is also described herein as an energy harvesting device 40). Typically, converter 40 comprises a transconductive material that converts mechanical energy into electrical energy. In many embodiments, energy converter 40 comprises a piezoelectric material which generates electrical energy in response to mechanical deformation of the converter. The converter 40 is desirably positioned in lead 30 to deform in response to motion from the heartbeat so that with each heartbeat, the converter deforms to generate electrical power to power pacemaker 20. Thus in these and related embodiments, converter 40 has a deformed and a non-deformed state.

Converter 40 can be sized or otherwise configured to generate sufficient electrical power to meet all of power needs of pacemaker 20 or to supplement the current from a pacemaker battery or other power supply, allowing for longer battery life as well as providing a backup should the pacemaker battery fail. Power management circuitry (described below) can be used to switch between use of battery power or the converter depending upon the charge level of the battery and/or the power requirements of the pacemaker or other device 20. In various embodiments, the converter can be configured to generate between 10 to 100 μamps of current with specific range of 20 to 40 μamps; greater and lesser ranges are also contemplated.

The thickness and material properties of converter 40 can be configured to have a stiffness/flexibility which allows for a peak generated voltage or other power generation characteristic that is matched to the normal physiological range of pulse rates e.g. 40 to 180 (which also corresponds to the rate of deformation of the converter). Other power generation characteristics which can be so matched include, root mean square generated voltage, peak generated current or root mean square generated current. In this way, the power generation characteristics of the converter can be optimized for use in pacing and various other cardiac applications. In other non-cardiac embodiments, the power generation characteristics can be matched to the frequency of other bio-kinetic events such as respiration rate.

For embodiments where converter 40 is placed on or in lead 30, the converter 40 can have a variety of shapes and spatial arrangements with respect to the lead. For example, the converter can have a cylindrical or rectangular shape that is coaxial with respect to longitudinal axis 30a of lead 30. Other shapes and arrangements are also contemplated. For example, the converter can comprise a tube or layer that is positioned over or within lead 30. The converter can also have a form factor or shape 40s, that does not appreciably change the form factor or shape 30s of lead 30. In this way, no additional volume is required for integrating the converter into the lead. In a preferred embodiment, converter 40 can have a rod shape 40r in its non-deformed state. In such embodiments, bending or flexing of the rod provides the deformation that causes the generation of electrical energy. The stiffness of the rod can be configured to cause selectable amounts of bending and produce a particular maximum voltage for a given frequency of deformation from a heart beat or other bio-kinetic event. Rod 40r or other shaped converter 40 can also be configured to generate electrical energy from multiple types of deformation such as bending twisting, pulling, compression and combinations therefore. Further, rod 40r or other energy converter 40 can be configured to generate electric power independent from a plane of deformation of the energy converter.

Rod 40r can also be tapered, articulated, crimped or otherwise configured to bend at particular location or locations so as to generate the maximum amount of voltage. As is shown in FIG. 1c, various embodiments of rod 40r or other converter 40 can have a stiffness profile 40sp configured to optimize the generation of voltage depending upon the position of the lead in the heart, position of the converter in the lead, heart rate or other factor. In the embodiment shown in FIG. 1c, the stiffness profile 40sp1 is configured to produce deformation near the mid portion of the converter rod. Other profiles are also contemplated, such as a stiffness profile 40sp2 with a maximum stiffness in the center of the rod and decreasing profiles towards the ends so as to produce a bending deformation along the entire length of the converter. In another embodiment, the converter can be configured to have a sinusoidal like stiffness profile along its length so as to produce a standing wave of bending motion and deformation. Stiffer profiles can be used for locations likely to produce greater amounts of deformation and vice versa. The stiffness profile can be selected to produce a resonant frequency which is within the range of physiological heart rates for the patient or a patient population to which the patient belongs.

Figure 1D:
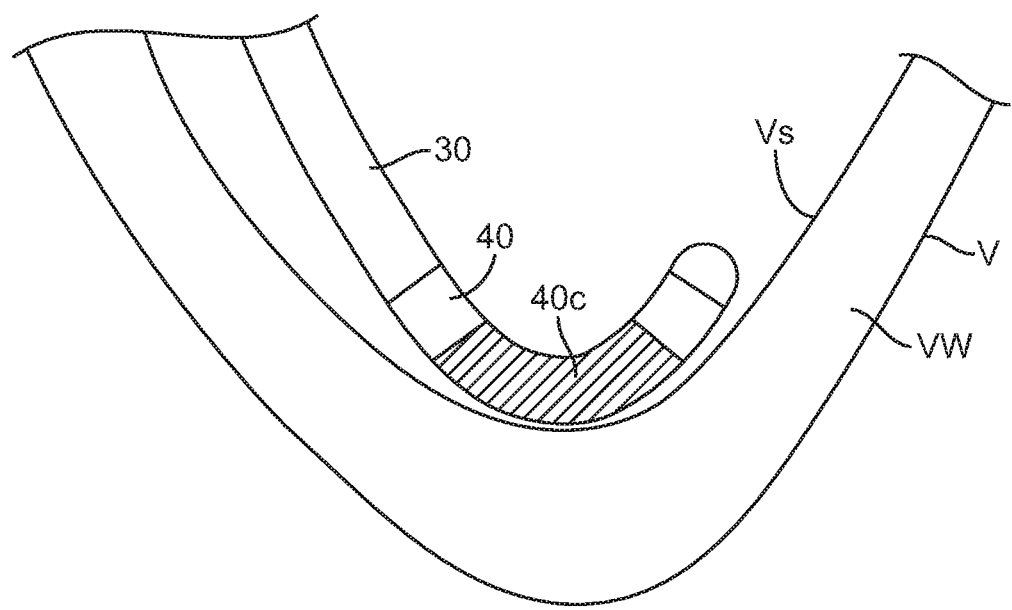
FIG. 1d is a lateral view showing an embodiment of a curved energy converter positioned in the ventricle.
Figure 2:
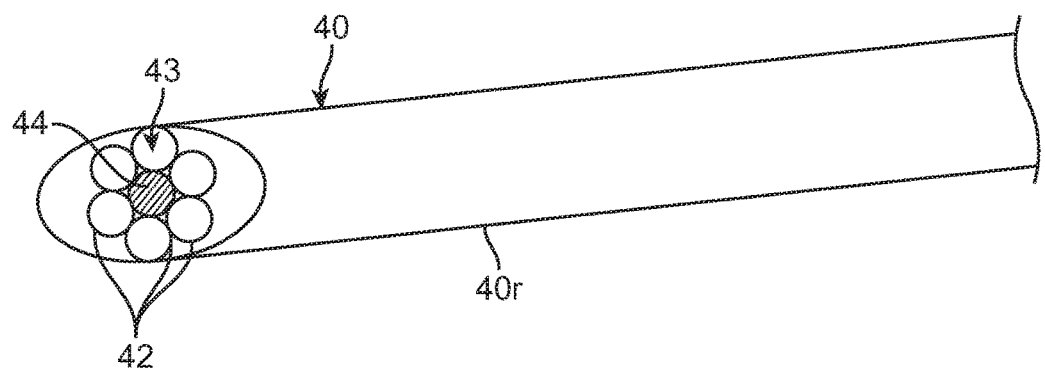
FIG. 2 is a perspective view illustrating an embodiment of an energy converter made up of a bundle of piezo-electric fibers.

In various embodiments, all or a portion of rod 40r can be pre-shaped to have a curve or other shape 40s with spring memory so that the rod will bend from motion of the heart or other bio-kinetic event and then spring back to its original shape. As is shown in FIG. 1d, the shape of the curve 40c can correspond to a shape Vs of the ventricular wall VW in its contracted or expanded state so that electrical energy can be generated during systole, diastole or both. In particular embodiments, ultrasound or other medical imaging methods can be used to determine the shape and degree of curvature of the patient's ventricular wall and then this image can be used to custom fabricate the shape 40s of converter 40 using medical product fabrication techniques known in the art. In use, such embodiments allow for increased amounts of converter deformation and thus voltage and power generation. Other shapes can be selected for positioning the converter in different locations in the body In many embodiments, converter 40 comprises a bundle 42 of piezo electric fibers 43 which are arranged around a core conductor 44. The piezo electric fibers are of a sufficient number and arrangement such that when bundle 42 is deformed in a given direction, at least one fiber 43 will be deformed sufficiently to generate sufficient energy for the pacemaker 20. In various embodiments, between 4 and 20 fibers can be symmetrically distributed around core 44, with specific embodiments of 6, 8, 10, 12, 14 and 16. In a preferred embodiment, bundle 42 has six fibers 43 symmetrically distributed around core 44. Also, preferably the diameter of fibers 43 is equal or less than that of core 44. In use, embodiments of bundle 42 allow for the generation of voltage and power by the converter from deformation in any direction. Further description of the use of piezoelectric fiber bundle as an energy converter is found in U.S. Provisional Patent Application Ser. No. 61/095,619, entitled ENERGY HARVESTING MECHANISM and U.S. patent application Ser. No. 12/556,524, entitled ENERGY HARVESTING MECHANISM; the aforementioned applications being fully incorporated herein by reference for all purposes. Other materials can also used for fibers 43 including various electret and peltier materials known in the art.

Figure 3A:
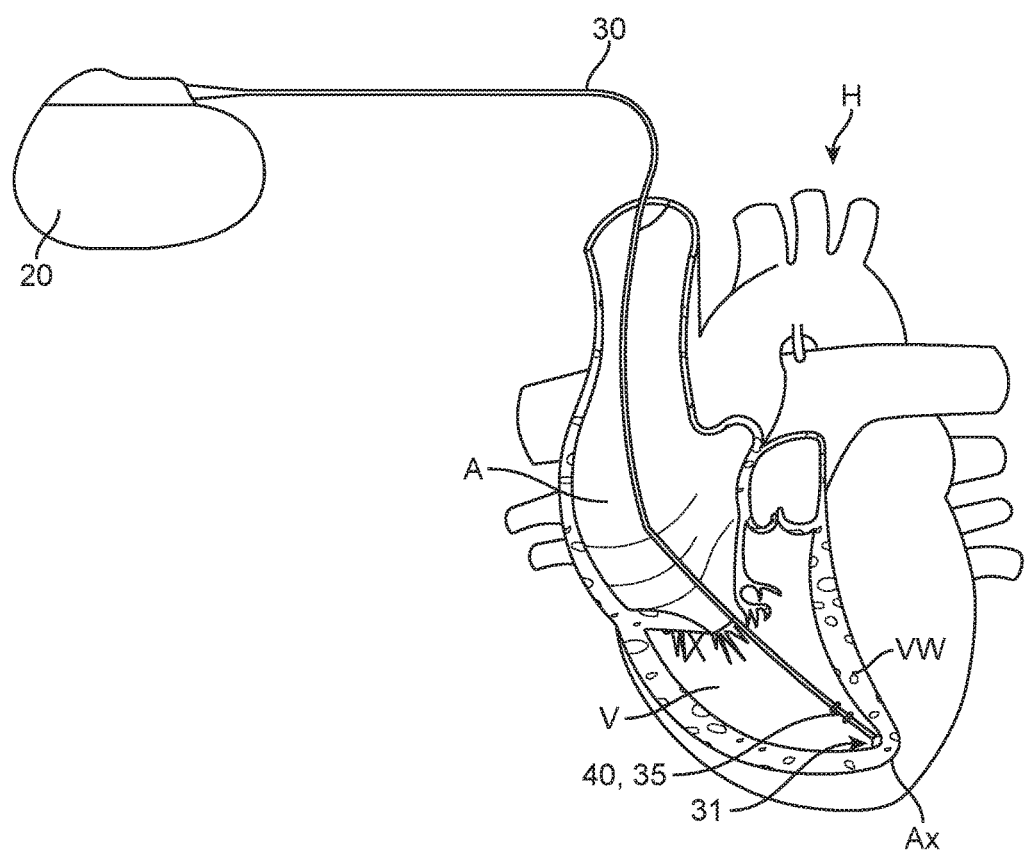
FIG. 3a is a lateral view showing an embodiment of an energy harvesting system for a cardiac pacemaker where energy is generated from deformation of a cardiac pacemaker lead containing an energy converter/energy harvesting device.
Figure 3B:
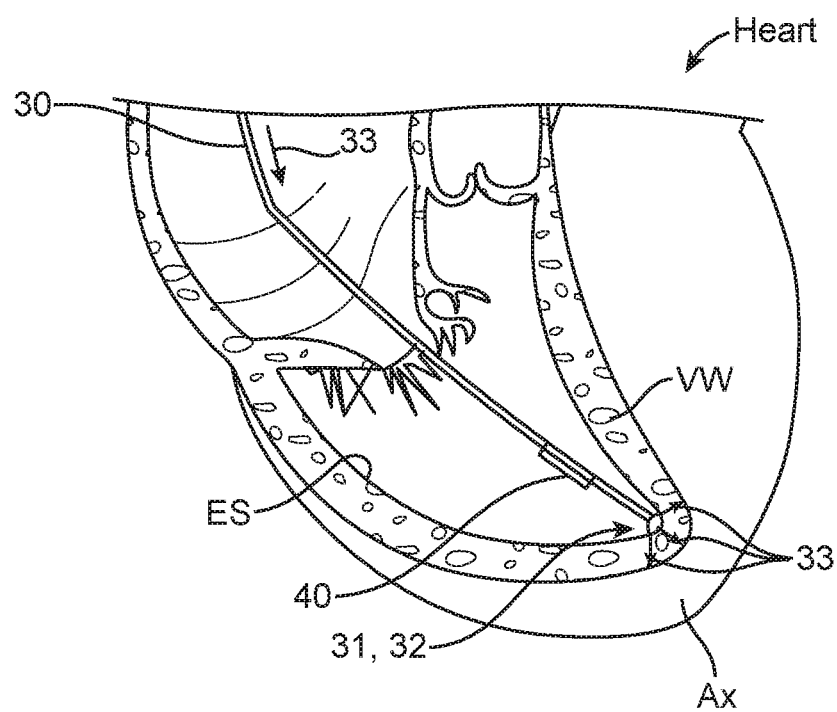
FIG. 3b is an expanded view of the embodiment of FIG. 3a showing the positioning of an energy harvesting pacemaker lead in the ventricle of the heart.
Figure 3C:
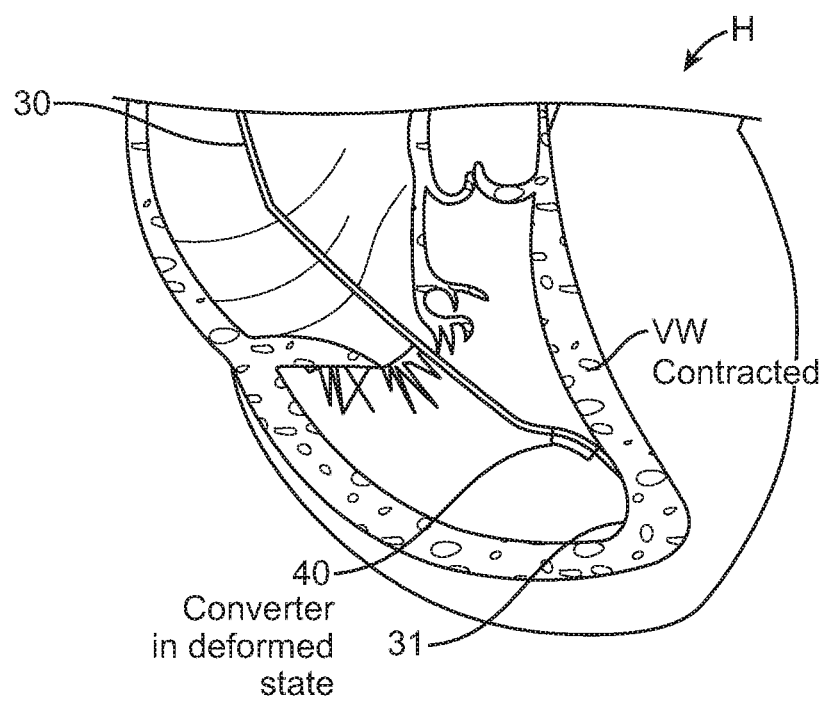
FIG. 3c is an expanded view of the embodiment of FIG. 3a showing the deformation of the pacemaker lead and energy converter caused by the contraction of the ventricle.

Referring now to FIGS. 3a-3d, typically lead is 30 positioned in ventricle V such that distal end 31 makes contact with the endocardial surface ES of the ventricular wall VW. This allows electrode 32 to be in electrical conduct with surface ES so as to conduct signal 33 to the ventricle of the heart (lead 30 can also be positioned in the atria of the heart so as to make contact with the atrial wall). In many cases, the distal end of the lead can include a fixation device (not shown) such as a helical tip that allows the lead to be fixed to the ventricular wall (as is shown in FIG. 3b) or other portion of the heart wall. The portion 35 of lead 30 containing energy converter 40 is desirably placed within a location in the ventricle V or other portion of the heart H so that it is flexed or otherwise deformed by the motion of the heart. For example, in the embodiment shown in FIG. 3b, the converter can placed in lead portion 35 that is positioned near the apex Ax of the heart. This allows the converter to be bent and otherwise deformed with each contraction of the ventricle as is shown in FIG. 3c. Lead 30 can also include multiple energy converters 40 positioned at selectable locations in the lead so as to have multiple locations for electrical energy generation. For example, the energy converter can include a first energy converter positioned in a first location and a second energy converter positioned at a second location. The first energy converter can be configured to generate energy during a first portion of the bio-kinetic event and the second energy converter configured to generate energy during a second portion of the bio-kinetic event. The bio-kinetic event can be a heartbeat, where the first portion of the event is systole and the second portion is diastole. Energy converter 40 can even be embedded into the ventricular wall itself (e.g., using a helical or other anchor) so as to be directly deformed by the motion of the heart. In such embodiments, the converter 40 is desirably fabricated from a flexible material so as to not mechanically impede the contractile motion of the heart. The converter 40 can be configured to have a stiffness profile that allows for maximum amounts of deformation of the converter during the course of a heart beat while minimizing any forces impeding contraction of the chambers of the heart such as the left ventricle. This can be achieved by configuring the bending stiffness of the converter to be less than the forces developed by the contracting chambers of the heart. In particular embodiments, the bending stiffness can be less than contractile forces of particular chambers of the heart (e.g., the left ventricle) by a factor in the range of 1.5 to 20 times, with specific embodiment of 2, 4, 6, 8, 10, 14, 16 and 18 times). Other ratios are also contemplated.

Figure 3D:
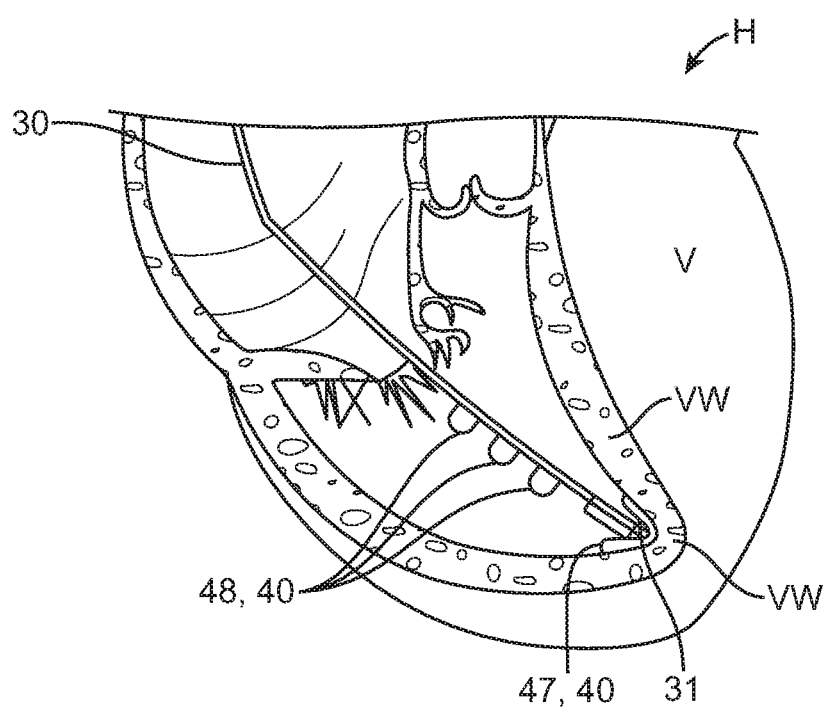
FIG. 3d is a lateral view showing an embodiment of an energy harvesting device comprising a patch or layer positioned adjacent the ventricular wall or a vane positioned on the cardiac pacemaker lead away from the ventricular wall.

Referring now to FIG. 3d, in other embodiments, converter 40 can comprise a thin patch or layer 47 that is attached to the distal end 31 of lead 30 and also rests against the ventricular wall VW. Layer 47 is desirably made of a very thin flexible material and is deformed each time the ventricle contracts and relaxes. Layer 47 can have a variety of shapes but is desirably circular or oval. In another embodiment, converter 40 can comprise a vane or blade 48 that is attached to lead 30. Vane 48 has a shape and size configured to be deformed by flowing blood in the ventricle (or atria) while minimizing blood cell lysis. In various embodiments, vane 40 can comprise a circular or oval shape. The vane can also be coated with one or more non-thrombogenic coatings known in the art (e.g., silicone, etc) including various drug eluting coatings.

Figure 4:
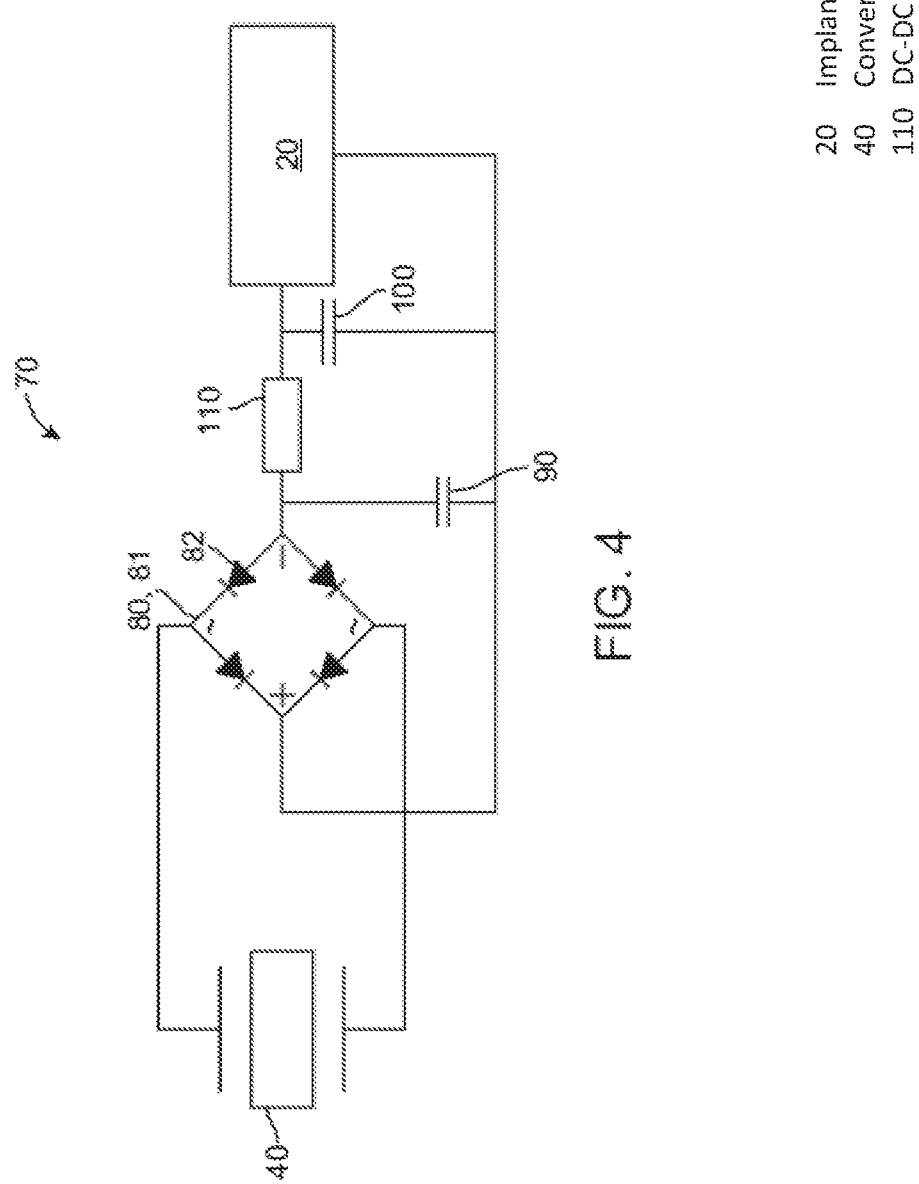
FIG. 4 is a schematic view illustrating an embodiment of a circuit architecture for converting power signals from an energy harvesting device for use by a cardiac pacemaker.
Figure 5:
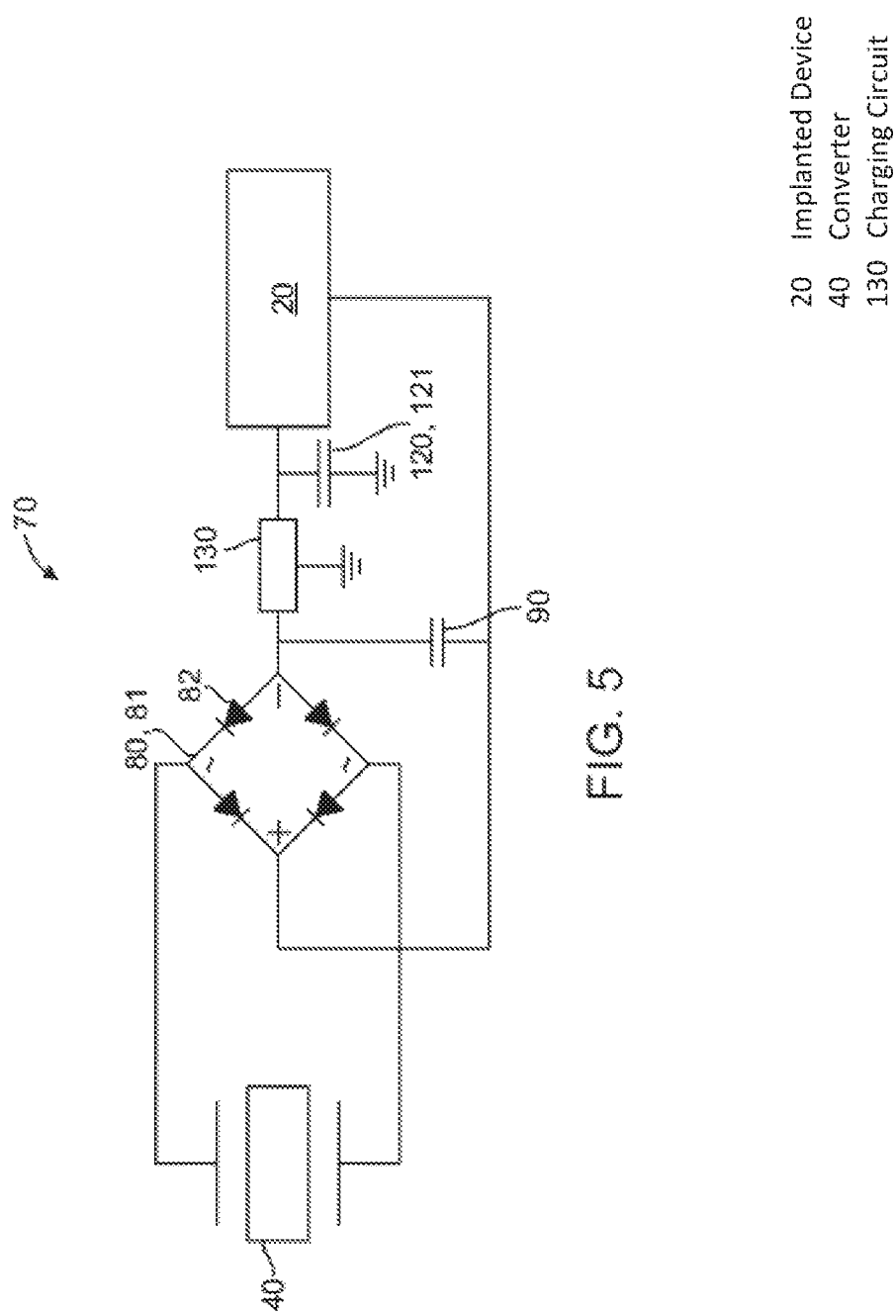
FIG. 5 is a schematic view illustrating an embodiment of an energy harvesting circuit architecture for powering a cardiac pacemaker where the architecture includes a rechargeable battery.
Figure 6:
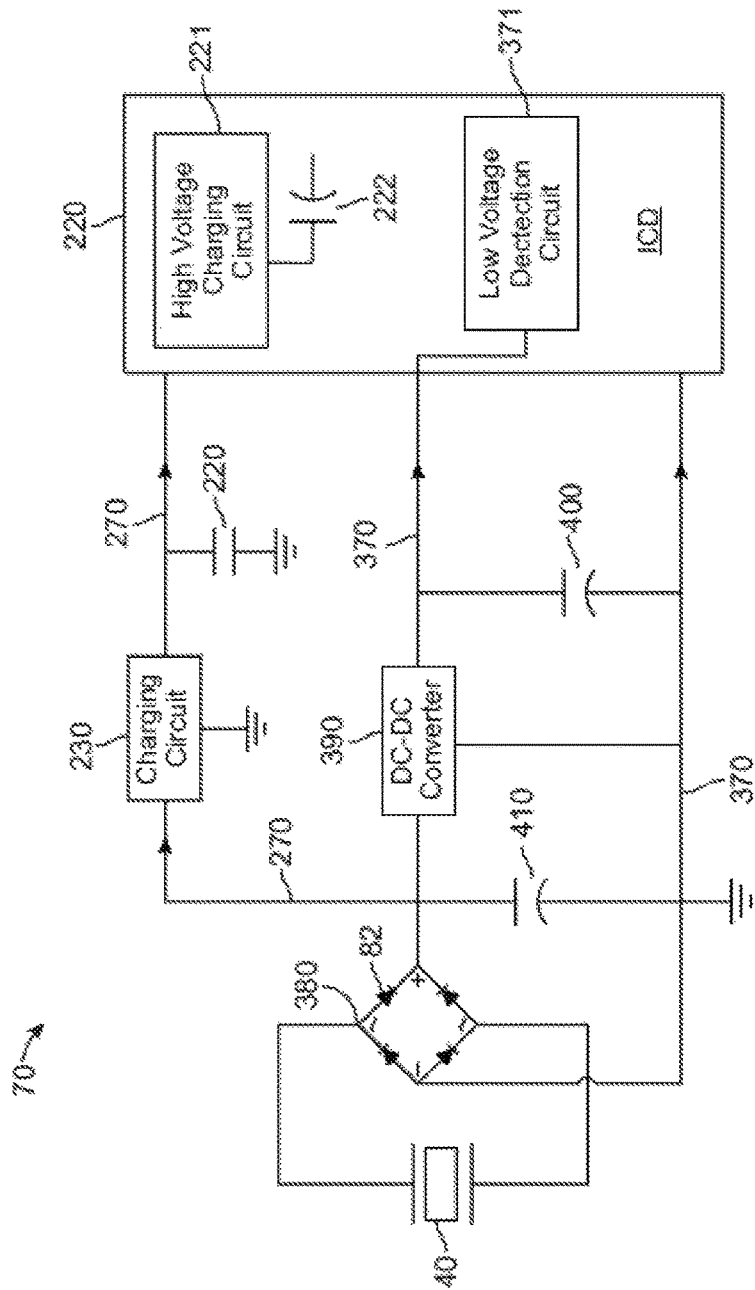
FIG. 6 is a schematic view illustrating an embodiment of a circuit architecture for converting power signals from an energy harvesting device for use by a cardiac defibrillator.

Referring now to FIGS. 4-6, various circuit architectures can be employed for utilizing energy from embodiments of harvesting energy devices described herein to power a cardiac device such as an implanted cardiac pacemaker or cardiac defibrillator. One embodiment of a circuit architecture 70 for using an energy harvesting device or converter 40 to power a cardiac pacemaker 20 is shown in FIG. 4. In this and related embodiments, architecture 70 can include converter 40, a rectifying circuit 80 for rectifying AC to DC voltage, a first capacitor 90, a second high value capacitor 100, a DC to DC converter 110 and pacemaking device 20. In many embodiments, the voltage generated by deformation of the converter 40 is AC and can be rectified to generate DC using a rectifying circuit 80. In preferred embodiments, circuit 80 can comprise a bridge circuit 81 using one or more Schottky diodes 82. Also, a DC to DC converter 110 can be used for stepping up or stepping down voltage for the pacemaker. Converter 110 can be linear, switch mode or magnetic. Capacitor 100 can have sufficient capacitance to power the pacemaker for short periods of time. In the embodiment shown, the pacemaker 20 has a power requirement of between 50-100 µw. Converter 40 can be configured to meet all or a portion of this power requirement. All or a portion of the components of architecture 70 can be contained in an application specific integrated circuit or ASIC.

In another embodiment shown in FIG. 5, architecture 70 can include a rechargeable power supply 120 such as a rechargeable battery 121, or like device along with charging circuitry 130. Suitable rechargeable batteries include nickel cadmium, lithium, lithium ion cell, lead acid and like chemistries. Power supply 120 can be configured to provide power for a selectable period should the patient's heart stop or develop an arrhythmia, or other condition which prevents adequate power generation by converter 40 for pacing or other function. Charging circuit 130 can include or otherwise be coupled to power management circuitry 135 that employs one or more power management regimens or algorithms 136 (via hardware or software). Power management circuitry 135 (see FIG. 7) and regimens 136 can be employed to recharge power supply 120 while still maintaining sufficient current and voltage for pacing. In one embodiment, a trickle charge regimen can be used. A duty cycle approach can also be employed to divert power during portions of the cardiac cycle that does not require pacing. In other embodiments, EKG monitoring circuitry can be used to determine when pacing is not required and then signal to the power management circuitry to divert power to the rechargeable power supply. A combination of these approaches can also be employed.

In another embodiment of an energy harvesting circuit architecture 70 shown in FIG. 6, architecture 70 can be configured to meet the power needs of an implantable cardiac defibrillator (ICD) device 220. In these and related embodiments, architecture 70 can include a high voltage architecture 270 and a low voltage architecture 370. High voltage architecture 270 is used to power a high voltage circuit 221 of defibrillator 220 that is in turn used to charge a defibrillator capacitor 222. Architecture 270 can include charging circuitry 230 and a rechargeable battery 220. Low voltage architecture 370 is used to power a low voltage circuit 371 of defibrillator 220 and can include a bridge circuit 380, a dc to dc converter 390 and a large value capacitor 400 and a capacitor 410.

Figure 7:
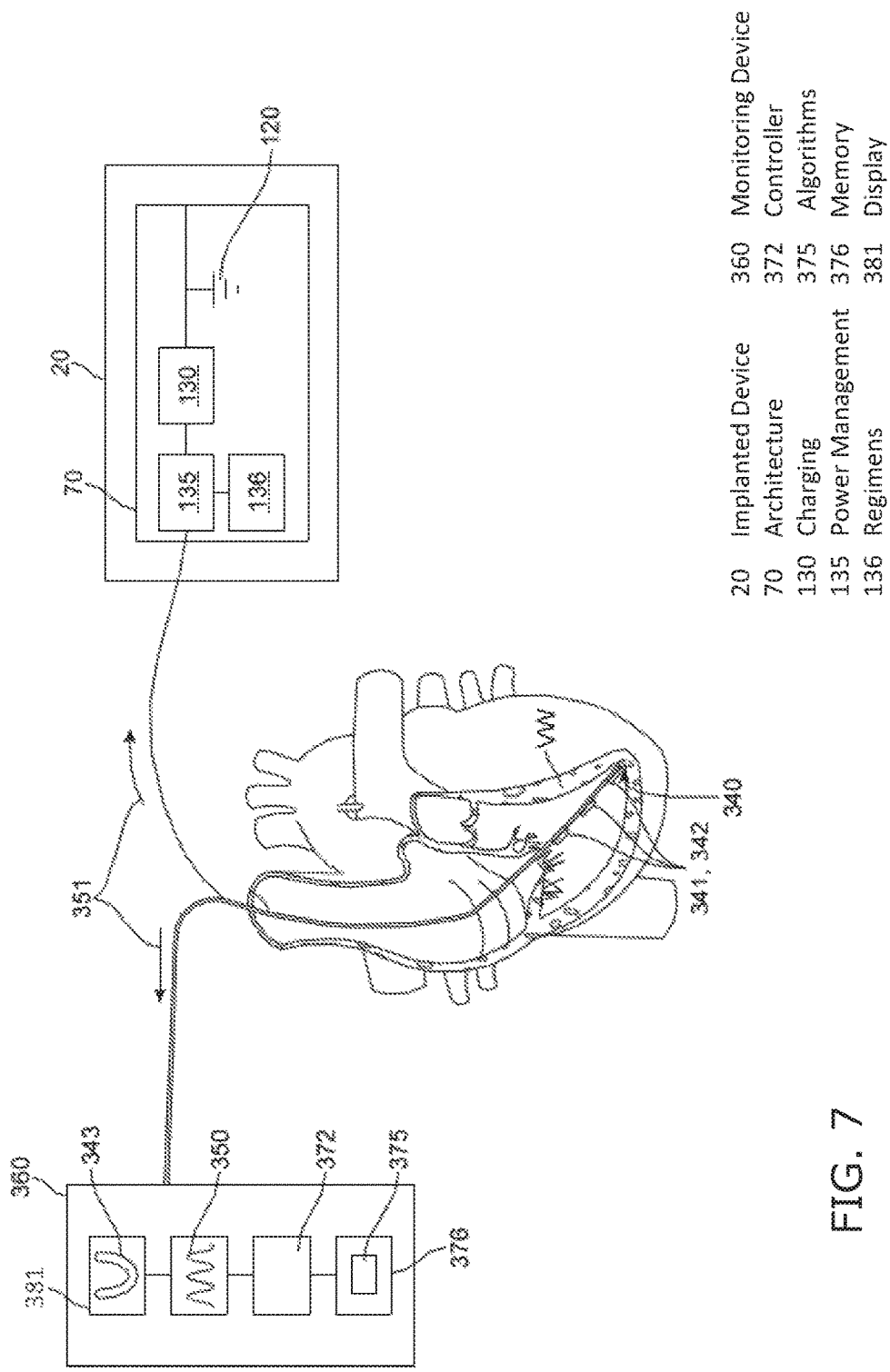
FIG. 7 is a lateral view illustrating use of an energy harvesting device as a sensor for detecting conditions of the heart.
Figure 8:
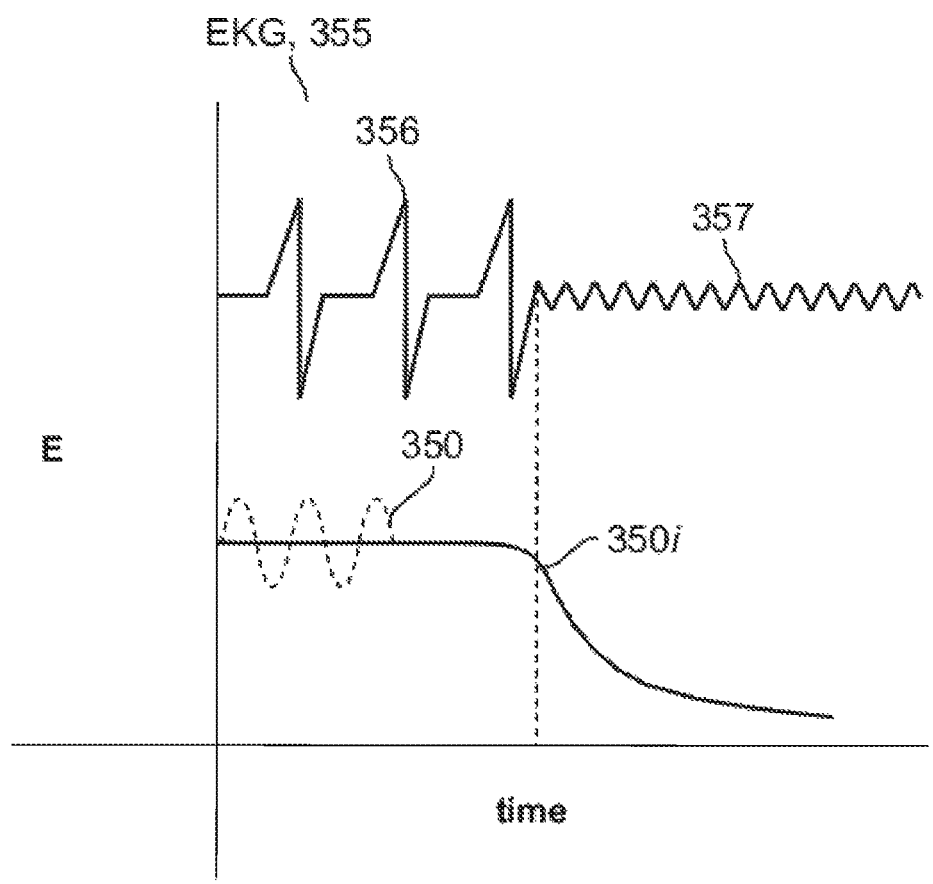
FIG. 8 shows an EKG and a corresponding electrical waveform generated by an energy harvesting device coupled to a pacemaker lead in the heart.

Referring now to FIGS. 7-8, in various embodiments, energy converter 40 can also be used as a sensor 340 to sense properties of the heart or other organ or tissue. Sensor 340 generates a voltage or other electrical waveform 350 that is produced by motion of the heart causing deformation of the sensor. Waveform 350 is affected by various characteristics of heart motion including heart rate and wall motion. These characteristic affect one or more of the frequency, amplitude and shape of the wave form. Accordingly, in addition to its use in powering cardiac pacemaker or other cardiac device 20, waveform 350 can be used to analyze and measure various properties of the heart. Such properties can include heart rate; rhythm (e.g., normal sinus rhythm (NSM) arrhythmia, pvc's, etc.) and wall motion abnormalities, myopathy, ventricular hypertrophy and related conditions. In the embodiment shown in FIG. 8, waveform 350, can be correlated to the patient's EKG 355 and used to analyze changes in the EKG to ascertain whether the heart is in normal sinus rhythm 356 or has gone into fibrillation 357. In the later case, fibrillation or other motion abnormality can be detected by a sudden decrease in the amplitude of voltage waveform 350 as may be indicated by an inflection point 350i in curve 350.

In various embodiments, sensor 340 can comprise a plurality 341 of sensors 340 that are placed at various locations along lead 30. The placement of sensors 340 can be in a pattern 342 so as to generate a map 343 of heart wall motion. Map 343 can be used to analyze heart wall motion including propagation of waves of contraction and relaxation in the heart wall along whole sections of the ventricle or atria. Map 343 can also be used to generate a wall motion score index for the mapped region of the ventricle. In one embodiment, the plurality 341 of sensors 340 can comprise at least three sensors that are positioned in lead 30 as to be located in the top, middle and apex portions of the heart. This allows for the detection of the wave of ventricular wall contractions as it moves from the apex through the upper/superior portions of ventricle. Time and/or phase lags between the waveforms 350 generated at each sensor 340 in the pattern can also be used to deduce various wall motion abnormalities such as regional akinesia.

Sensor 340 can be coupled to a monitoring device 360 which includes a controller 372 and a display 381. Sensor 340 signals a waveform signal 351 to device 360 and controller 372. Controller 372 can include one or more algorithms 375 resident in memory resources 376 coupled to the controller for analyzing signal 351. Suitable memory resources include RAM, ROM, DRAM and other electronic memory resources known in the art. Algorithms 375 can analyze one or more of the voltage, current or power wave forms generated by sensor 340. Specific embodiments of algorithms 375 can be configured to detect changes in amplitude, frequency of wave form 350 or both. Detection and analysis of these changes can be used both for patient diagnostic and power management purposes. For example, when the amplitude (e.g., voltage) or frequency of the waveform falls below a threshold, a signal can be sent to a controller or telemetry circuit coupled to or resident within device 20 to alert the patient or medical professional. Signals can also be sent to power management circuitry 135 to switch to battery power from battery 120 or other power supply. Changes in waveform 350 can also be detected using derivative or integral functions. For example, a derivative function can be used to look for rates of change in amplitude. An integral function can be used on one or more curves, for example, to look for changes in total work done over time. Other numerical methods and pattern recognition algorithms known in the art can also be employed (e.g., fourier analysis. fuzzy logic algorithms, etc.)

In various embodiments, sensor 340 and/or device 20 can include an RF communication chip or like device for wirelessly signaling device 360 using BLUE TOOTH or other RF communication protocol. Other means of medical telemetry known in the art are also contemplated. In these and related embodiments, monitoring device 360 can be worn by the patient or placed within proximity of the patient. It may also be integrated into various portable communication devices such as cell phones, PDA's and like devices that the patient wears or places in proximity to their person. In these and related embodiments, when a condition warranting alerting of the patient is detected (e.g., an arrhythmia), a signal is sent to device 360, device 360 can concurrently sound an alarm and also send a signal over a wireless phone or other network (e.g., the Internet) to alert the patients doctor, nurse or other medical care provider.

CONCLUSION

The foregoing description of various embodiments of the invention has been presented for purposes of illustration and description. It is not intended to limit the invention to the precise forms disclosed. Many modifications, variations and refinements will be apparent to practitioners skilled in the art. For example, various embodiments of the energy harvesting mechanisms can be sized and otherwise adapted for placement in variety of locations in the body including without limitation the abdominal cavity, the chest cavity and the extremities and adapted to utilized particular bio-kinetic events in those locations such as peristaltic waves, respiration/diaphragm movement or any number of muscle contractions or movement of a limb. Various embodiments can also be configured placed in the heart or arterial system to utilize an arterial pulse to produce deformation of the energy converter. Also, embodiments of the energy harvesting mechanism can be sized or otherwise adapted for various pediatric and neonatal applications.

Elements, characteristics, or acts from one embodiment can be readily recombined or substituted with one or more elements, characteristics or acts from other embodiments to form numerous additional embodiments within the scope of the invention. Moreover, elements that are shown or described as being combined with other elements, can, in various embodiments, exist as standalone elements. Hence, the scope of the present invention is not limited to the specifics of the described embodiments, but is instead limited solely by the appended claims.

What is claimed is:

1. An energy harvesting mechanism for a pacemaker, the mechanism comprising:
    a deformable energy converter positionable inside a human body to convert a mechanical deformation of the energy converter by a bio-kinetic event of the human body into electric power signals, the energy converter having a stiffness profile in which a center portion of the energy converter has a stiffness that is greater than a stiffness at either end portion of the energy converter, and wherein the stiffness profile enables the energy converter to be deformable at either of the end portions; and
    a signal path component structured to enable the electric power signals to be carried from the energy converter to the pacemaker.

2. The mechanism of claim 1, wherein the pacemaker is a cardiac pacemaker.

3. The mechanism of claim 1, wherein the signal path component comprises a cable that provides a pace making signal to a heart of the human body.

4. The mechanism of claim 1, wherein the stiffness profile produces a resonant frequency within a predetermined physiological frequency range associated with a normal occurrence of the bio-kinetic event.

5. The mechanism of claim 3, wherein the energy converter is positioned within the cable.

6. The mechanism of claim 5, wherein the energy converter has a form factor which does not change a form factor of the cable.

7. The mechanism of claim 1, wherein the energy converter is structured to approximate a shape of a ventricle of the human body in a contracted or an expanded state so that the electric power signals can be generated during both systole and diastole.

8. The mechanism of claim 1, wherein the energy converter comprises a piezoelectric material.

9. The mechanism of claim 1, wherein the bio-kinetic event is a heartbeat, a respiration or an arterial pulse.

10. The mechanism of claim 1, wherein the energy converter functions as a sensor to sense a property of a heart of the human body.

11. The mechanism of claim 10, wherein the property is one of a heart rate, heart rhythm, arrhythmia, heart wall motion or heart wall motion abnormality.

12. The mechanism of claim 1, further comprising: a rechargeable power supply coupled to the signal path component to receive electrical energy generated by the energy harvesting mechanism.

13. The mechanism of claim 1, wherein the energy converter generates an AC signal.

14. The mechanism of claim 1, wherein the energy converter generates sufficient power to autonomously power the pacemaker from motion of a beating heart.

* * * * *